(12) United States Patent
Hagiwara et al.

(10) Patent No.: US 10,828,264 B2
(45) Date of Patent: Nov. 10, 2020

(54) ADHESIVE SKIN PATCH

(71) Applicant: Nichiban Co., Ltd., Tokyo (JP)

(72) Inventors: Isao Hagiwara, Tokyo (JP); Reona Koike, Tokyo (JP)

(73) Assignee: NICHIBAN CO., LTD., Tokyo (JP)

( * ) Notice: Subject to any disclaimer, the term of this patent is extended or adjusted under 35 U.S.C. 154(b) by 0 days.

(21) Appl. No.: 16/333,648

(22) PCT Filed: Sep. 13, 2017

(86) PCT No.: PCT/JP2017/033121
§ 371 (c)(1),
(2) Date: Mar. 15, 2019

(87) PCT Pub. No.: WO2018/052039
PCT Pub. Date: Mar. 22, 2018

(65) Prior Publication Data
US 2019/0209485 A1    Jul. 11, 2019

(30) Foreign Application Priority Data

Sep. 16, 2016    (JP) .................................. 2016-181855

(51) Int. Cl.
| | | |
|---|---|---|
| *A61K 9/70* | (2006.01) | |
| *A61K 9/00* | (2006.01) | |
| *A61K 47/34* | (2017.01) | |
| *A61K 31/167* | (2006.01) | |
| *A61P 25/02* | (2006.01) | |
| *A61K 47/12* | (2006.01) | |
| *A61K 47/44* | (2017.01) | |
| *A61P 23/02* | (2006.01) | |

(52) U.S. Cl.
CPC .............. *A61K 9/7023* (2013.01); *A61K 9/70* (2013.01); *A61K 9/7046* (2013.01); *A61K 31/167* (2013.01); *A61K 47/12* (2013.01); *A61K 47/44* (2013.01); *A61P 23/02* (2018.01)

(58) Field of Classification Search
None
See application file for complete search history.

(56) References Cited

U.S. PATENT DOCUMENTS

| | | | | |
|---|---|---|---|---|
| 5,292,697 A | * | 3/1994 | Klotz | ....................... B01J 29/04 423/12 |
| 6,953,590 B1 | | 10/2005 | Owaki et al. | |
| 2014/0171509 A1 | | 6/2014 | Mori et al. | |
| 2014/0356412 A1 | | 12/2014 | Mori et al. | |
| 2017/0348246 A1 | * | 12/2017 | Tohara | ................... A61K 45/00 |

FOREIGN PATENT DOCUMENTS

| | | |
|---|---|---|
| JP | 09-122221 A | 5/1997 |
| JP | 2016-3196 A | 1/2016 |
| WO | 2011-027786 A1 | 3/2011 |
| WO | 2012-029097 A1 | 3/2012 |
| WO | WO-2016103999 A1 * 6/2016 | ............. A61K 45/00 |

\* cited by examiner

*Primary Examiner* — Kyung S Chang
(74) *Attorney, Agent, or Firm* — Porter Wright Morris & Arthur LLP

(57) ABSTRACT

A nonaqueous adhesive skin patch at least comprises a backing film and an adhesive layer placed thereabove, the adhesive layer containing a local anesthetic, wherein when the total mass of an adhesive is set to 100% by mass, the adhesive layer includes the following in the ratio of: 20 to 40% by mass of an elastomer; 20 to 35% by mass of a softener; 20 to 40% by mass of a resin; 3.0 to 7.0% by mass of the local anesthetic; and 0.3 to 4.0% by mass of organic acid, and wherein the adhesive layer has a mass per unit area of 100 to 200 g/m².

8 Claims, No Drawings

ADHESIVE SKIN PATCH

TECHNICAL FIELD

The present invention relates to a nonaqueous adhesive skin patch containing a local anesthetic in an adhesive layer, and specifically it relates to a nonaqueous adhesive skin patch that can minimize the removed amount of keratin and can control the skin permeability of local anesthetics such as lidocaine.

BACKGROUND ART

Lidocaine, which is one type of local anesthetic, is used as local anesthesia for various body parts. It is used as a surface anesthetic agent that temporarily paralyzes nerves so as not to cause pain. For example, lidocaine may be used as an external preparation in the form of an ointment, jelly, spray, etc. and applicable as a surface anesthetic agent to, for example, postherpetic neuralgia. However, the external preparation in the form of an ointment, jelly or spray cannot be used while stably maintaining their effects thereof over a prolonged period of time. Accordingly, for achieving prolonged-pain reduction, adhesive skin patches containing lidocaine as local anesthetics have been developed. These adhesive skin patches come in the form of both aqueous adhesive skin patches and nonaqueous adhesive skin patches.

As aqueous adhesive skin patches containing lidocaine, LIDODERM (Registered trademark) of Endo Pharmaceuticals Inc. in the USA is well-known and is used as surface anesthesia for, for example, postherpetic neuralgia or as pain relief for various muscles. However, in the case of the aqueous adhesive skin patches, since these patches contain moisture, the skin fitness thereof has not been satisfied. Further, due to the inclusion of moisture, adhesion of those patches is weak causing the problem that the patches are not bearable for prolonged affixing. Yet further considering the aqueous adhesive skin patches, it has been noted that about 95% of lidocaine may remain in the patches after use, so that problems due to releasability and transdermal absorption of lidocaine have been presented.

For nonaqueous adhesive skin patches containing lidocaine, Penles (Registered trademark) of Maruho Co., Ltd. is well-known and is used for relieving pain when inserting an intravenous indwelling needle, when removing contagious molluscum, and when conducting skin-laser irradiation therapy. In accordance with the documents attached, Penles is used as follows: it is affixed to the body part where an intravenous indwelling needle is to be inserted, for about 30 minutes; Penles is then removed therefrom; and immediately after the remove, treatment such as the usage of the intravenous indwelling needle is performed. Further, when attempting to relieve pain at the time of the contagious molluscum removal and the skin-laser irradiation therapy, it is said that Penles is affixed to the body part to be treated for about 1 hour, and treatment is then performed. Penles (Registered trademark) is the preparation expected to have a prompt local anesthetic effect on a local body part, and it is not thus intended for the usage of prolonged affixation to skin.

The patent document, which discloses nonaqueous adhesive skin patches containing lidocaine, proposes, for example, that an adhesive layer is made to contain organic acid in addition to thermoplastic elastomer, liquid paraffin and tackifier. With the adhesive layer thus structured, a transdermal absorption preparation, which is designed to control transdermal absorbability, is proposed. (see Patent Document 1)

However, in the transdermal absorption preparation of Patent Document 1, the mass per unit area of the adhesive layer is 1000 $g/m^2$, resulting in a thick layer. This consequently makes the mass of lidocaine per unit area high, so as to give the preparation a high medication content. Cost-related problems will thus arise.

Considering another nonaqueous adhesive skin patch containing lidocaine, there is the proposal of the transdermal absorption preparation in which an adhesive layer is arranged with two types of acrylic copolymers, and organic acid to promote the crosslinking of the copolymers (see Patent Document 2).

Also, there is the disclosure of the transdermal absorption preparation, which contains lidocaine, lactic acid, thermoplastic elastomer and liquid paraffin (see Patent Document 3).

PRIOR ART DOCUMENTS

Patent Documents

[Patent Document 1] International Publication No. 2012/029097
[Patent Document 2] International Publication No. 2011/027786
[Patent Document 3] Japanese Patent Application Laid-open No. 2016-3196

SUMMARY OF INVENTION

Problems to be Solved by Invention

The present invention relates to the nonaqueous adhesive skin patch where an adhesive layer contains local anesthetics. Further, the purpose of the present invention is to provide the nonaqueous adhesive skin patch where: the skin permeability rate of medication is in a proper range when the patch is affixed so that effect on the medication does not wear off at the early stage of application; continuous medication permeation is possible for a prolonged period of time; the removed amount of keratin is limited when releasing the patch; and the patch is storable in a stable manner (good storage stability).

Means to Solve Problems

As a result of extensive studies in order to solve the above problems, the present inventors have found the following. Through the sufficient study of elastomers, softeners, resins, and local anesthetics, which each constitute the adhesive layer of nonaqueous adhesive skin patches, through further study of the formulation of organic acids, and by arranging the mass (thickness) of the adhesive layer to be within the predetermined range, it will be possible to obtain the continuous skin permeation of medication even without providing a high concentration of the blended amount of local anesthetics. Further, the present inventors have also found that the keratin remove amount can be reduced at the time of patch remove, and the good storage stability of the patch is guaranteed as well.

The present invention provides the following embodiment in the adhesive skin patch.

(1) It is a nonaqueous adhesive skin patch at least comprising a backing film and an adhesive layer placed thereabove, the adhesive layer containing a local anesthetic, wherein when the total mass of an adhesive is set to 100% by mass, the adhesive layer includes the following in the ratio of: 20 to 40% by mass of an elastomer; 20 to 35% by mass of a softener; 20 to 40% by mass of a resin; 3.0 to 7.0% by mass of the local anesthetic; and 0.3 to 4.0% by mass of a divalent or trivalent organic acid, and wherein the adhesive layer has a mass per unit area of 100 to 200 g/m$^2$.

In particular, the present invention provides the following embodiments in the adhesive skin patches.

(2) It is the nonaqueous adhesive skin patch shown in (1) of the above, wherein the organic acid is either a citric acid or a tartaric acid.

(3) It is the nonaqueous adhesive skin patch shown in (1) or (2) of the above, wherein the adhesive layer contains 25 to 35% by mass of the softener and 30 to 40% by mass of the resin.

(4) It is the nonaqueous adhesive skin patch shown in (1) to (3) of the above, wherein the adhesive skin patch contains the local anesthetic in an amount such that a cumulative permeation amount of the local anesthetic after an elapse of 12 hours since application is 120 to 200 μg/cm$^2$.

(5) It is the nonaqueous adhesive skin patch shown in (1) to (3) of the above, wherein the adhesive skin patch contains the local anesthetic in an amount such that a cumulative permeation amount of the local anesthetic after an elapse of 12 hours since application is 150 to 200 μg/cm$^2$.

(6) It is the nonaqueous adhesive skin patch shown in (1) to (5) of the above, wherein the local anesthetic is lidocaine.

(7) It is the nonaqueous adhesive skin patch shown in (1) to (6) of the above, wherein the resin is a hydrogenated rosin glycerin ester.

(8) It is the nonaqueous adhesive skin patch shown in (1) to (7) of the above, wherein the adhesive layer does not contain an antioxidant and a transdermal absorption accelerant.

(9) It is the nonaqueous adhesive skin patch shown in (1) to (8) of the above, wherein the patch is applicable for postherpetic neuralgia.

(10) It is the nonaqueous adhesive skin patch shown in (1) to (9) of the above, wherein the backing film is a polyester knit fabric.

(11) It is the nonaqueous adhesive skin patch shown in (1) to (10) of the above, wherein 10 to 84 mg of the organic acid is blended per one preparation of the nonaqueous adhesive skin patch.

Effect of Invention

According to the present invention, the continuous skin permeation of local anesthetics can be realized. Further, the present invention can realize a weak-acid adhesive layer and can reduce skin irritation by suppressing the remove amount of keratin. Still further, the present invention can provide a nonaqueous adhesive skin patch while maintaining good storage stability.

EMBODIMENTS TO CARRY OUT THE INVENTION

In adhesive skin patches containing local anesthetics (for example, the lidocaine-containing preparation described above), it surely needs to satisfy basic requirements that have conventionally been viewed as standard in such patches (for example, adhesibility to skin or suppressibility of skin irritation). However, from the viewpoint of safety in application, the skin permeation rate of medication at the initial stage of application should be appropriate. More specifically, it is important that the risk of side-effects such as abnormal medication permeation or a sharp rise in blood-concentration should be limited at the application sites (damaged skin etc.). In addition, considering the nature of the preparation, it is important that the medication will not wear off before the end of the applied period, within the assumed applicable period (the period the patch is affixed). Further, it is also important that the appropriate amount of medication is continuously permeated (infiltrated) into the skin. Still further, considering the adhesive skin patch after application, it is also desired that the remaining amount of medication is minimized (eventually improving medication efficiency).

There has been a proposal to, for example, combine a dissolving agent such as organic acid or polyhydric alcohol in order to optimize the skin permeation rate of the medication (local anesthetic). However, this may create the risk of skin disorders or have a negative effect on the adhesion properties of the adhesive skin patch when the blended amount of the dissolving agent is large. Note that, even if the blended amount of the dissolving agent is at the assumed normal level, depending on its formulation, skin permeation control may become excessive, so that it may largely suppress the medication permeation or may excessively increase the medication permeation.

Furthermore, it is assumed that the local anesthetic-containing adhesive skin patch needs to be repeatedly applied to the diseased part at least for a certain period of time, so that skin irritation when the patch is affixed needs to be limited as far as is possible. In addition, it is required that irritation when and after releasing the patch, as well as keratin remove, needs to be minimized as much as possible.

In an actual use environment, not only should the preparation be stable during application, but the preparation should not be allowed to deteriorate even in a somewhat harsh storage environment (showing good storage stability).

The inventors of the present invention have diligently studied various requirements for the above-mentioned adhesive skin patch that contains local anesthetic, specifically, basic requirements of adhesive skin patches (adhesibility, etc.), realization of the adequate medication amount in skin permeation from the beginning to the end of application, the improvement of medication efficiency, the suppression of skin irritation during and after the application of the patch, and the improvement of storage stability. In addition, the inventors have strictly examined the blending amount of each component constituting the adhesive layer. As a result, the inventors have found that, especially by combining resins, softeners and further organic acids (for example, citric acid) in the predetermined blending amount range, it can achieve continuous skin permeation through the appropriate amount of medication. Further, it is also realized that skin irritation due to keratin remove is also reduced.

Especially, by setting the cumulative permeation amount of medication up to 12 hours after application to be in the prescribed range such as: about 120 to 200 μg/cm$^2$, preferably about 150 to 200 μg/cm$^2$, the inventors have found the following: the skin permeation performance of medication is appropriate even after the elapse of a certain period of time; the generation of the risk of side-effects or skin irritation due to excessive initial medication permeation (for example, rapid increase in blood concentration) can be reduced; and the occurrence of medication wear-off at the end of application can be suppressed. Note that the cumulative permeation amount after 12 hours of application of the lidocaine-containing aqueous adhesive skin patch (LIDODERM (Registered trademark)) is around 150 to 200 μg/cm$^2$.

In the preparation of LIDODERM (Registered trademark), about $30 \times 10^{-5}$ mol/cm$^2$ per area of lidocaine is required while about $2 \times 10^{-5}$ mol/cm$^2$ per area of lidocaine is required in the prior art (Patent Document 1). However, by adopting the above constitution, even if the lidocaine is reduced by a factor of 10, for example, about $0.3 \times 10^{-5}$ mol/cm$^2$, or even about $0.25 \times 10^{-5}$ mol/cm$^2$, it is possible that about the same level of sufficient medication permeation can be realized while improving the usage efficiency of medication.

Hereinafter, each component constituting the present invention will be described in detail.

<Adhesive Skin Patch>

The present invention is a nonaqueous adhesive skin patch at least comprising a backing film and an adhesive layer placed thereabove, the adhesive layer containing local anesthetics.

<Adhesive Layer>

[Rubber-Based Elastomer]

In the adhesive layer of the nonaqueous adhesive skin patch of the present invention, rubber-based elastomers are used as the base component. Examples of the rubber-based elastomers include: thermal plastic block copolymers such as a styrene-isoprene-styrene copolymer (hereinafter may be referred to as "SIS"), a styrene-butadiene-styrene copolymer (hereinafter may be referred to as "SBS"), or these hydrogenated products, a styrene-ethylene-propylene-styrene copolymer (hereinafter may be referred to as "SEPS"), and a styrene-ethylene-butylene-styrene copolymer (hereinafter may be referred to as "SEBS"); an ethylene-vinyl acetate copolymer; various thermoplastic elastomers such as ethylene-a-olefin copolymer, polyisoprene, polyisobutylene, butyl rubber, liquid rubber and the like. These rubber-based elastomers may be used individually or in combination of two or more kinds thereof.

In the nonaqueous adhesive skin patch at which the present invention aims, the content of elastomers (in total) is not particularly limited, but it is generally from 15 to 50% by mass, preferably from 20 to 40% by mass, for example, 25 to 40% by mass, 25 to 35% by mass, 30 to 35% by mass, alternatively 30 to 40% by mass or 35 to 40% by mass, when the total mass of the adhesive layer is set to 100%.

<Styrene-Based Thermoplastic Elastomer>

Among the above rubber-based elastomers, styrene-based thermoplastic elastomers, which are the thermoplastic block copolymers such as SIS, SBS, SEPS, SEBS and the like, are suitably used since they are excellent in tackiness and cohesiveness.

In particular, the SIS can provide elasticity and tackiness to the adhesive layer (plaster layers) while it can retain each component in the adhesive layer and can dissolve or disperse the other components. Accordingly, the SIS is especially suitable for the adhesive layer of the nonaqueous adhesive skin patch to achieve the present invention.

Although the SIS used in the present invention is not particularly limited, in general, the mass ratio between styrene and isoprene (styrene/isoprene) will be 10/90 to 30/70, preferably 20/80 to 25/75, when the total mass of the styrene and isoprene is set to 100 parts by mass. Thus, by using the SIS block copolymer with the large mass ratio of isoprene, it makes easier to produce the rubber-based adhesives.

Commercially available styrene-isoprene-styrene block copolymers may be used for the SIS. The example of a high-diblock ratio copolymer is Quintac 3520 (Nippon Zeon Co., Ltd.) while the examples in a low-diblock ratio copolymer include JSR SIS 5002 (JSR Corporation) and JSR SIS 5008 (JSR Corporation).

When two or more kinds of elastomers are used in combination, the content of the styrene-isoprene-styrene block copolymer is not particularly limited, but it may be, for example, 10 to 30% by mass or 15 to 30% by mass, and more preferably 15 to 25% by mass or 20 to 30% by mass.

<Polyisobutylene>

Among the above rubber-based elastomers, polyisobutylene may be used for obtaining compatibility in the adhesive layer during production processes and for retaining a highly polymerized compound with a low molecular weight in plaster.

Commercially available polyisobutylenes may be used as the polyisobutylene described above. For examples, as medium molecular-weight polyisobutylenes, the following may be mentioned: Opanol B-30, B-30SF, B-50 and B-80 (by BASF Japan Ltd.). On the other hand, as low molecular-weight polyisobutylenes, Opanol B-10, B-12, B-12 N, B-12 SFN, B-15 (by BASF Japan Ltd.), Vistanex LM-MS, LM-MH and LM-H (Exxon), Himores 4H, 5H, 5.5H, 6H, Tetrax 3T, 4T, 5T, and 6T (by JX Nippon Oil & Energy Ltd.) and the like may be mentioned.

<Other Rubber-Based Elastomers>

For example, in a case where the aforementioned SIS and polyisobutylene are used in combination as the elastomer component, liquid rubbers may be used to improve its compatibility. Examples of the liquid rubbers include polybutene, high cis-polyisoprene rubber, liquid polyisoprene rubber, and the like. Among these liquid rubbers, the high cis-polyisoprene rubber or liquid polyisoprene rubber will be preferable. One kind of the liquid rubber may be individually used, and two or more kinds thereof may be used in combination. When these liquid rubbers are used, the amount used may be 0.1 to 5% by mass, for example 0.3 to 3% by mass, when the total mass of the adhesive layer is set to 100% by mass.

[Local Anesthetics]

Examples of the local anesthetics to be contained in the adhesive layer of the present invention include lidocaine, bupivacaine, mepivacaine, ropivacaine, levobupivacaine, procaine, dibucaine, tetracaine and salts thereof. Among those local anesthetics, lidocaine will be preferable when considering side effects and the like. In the present invention, unless otherwise specified, lidocaine and pharmacologically acceptable salts thereof are indicated. Each content of the local anesthetics is generally 1.5 to 10.0% by mass with respect to the total mass of the adhesive layer. Note that, from the viewpoints of the effects, the risk of side-effects as well as the medication efficiency of the local anesthetics, the content of the local anesthetics may be 3.0 to 7.0% by mass, for example 3.5 to 6.0% by mass, alternatively 4.0 to 6.0% by mass or 4.0 to 5.0% by mass.

[Resin]

The adhesive layer of the nonaqueous adhesive skin patch of the present invention may be combined with resin in order to control adhesion to be suitable.

Examples of the resin include rosin resin, rosin ester resin, other rosin derivative resins, terpene phenol resin, coumarone-indene resin, dicyclopentadiene petroleum resin and the like. Among these, hydrogenated rosin glycerin esters and terpene resins are preferably used, and commercially available products include Pine Crystal KE-311 (manufactured by Arakawa Chemical Industries, Ltd.), YS resin (manufactured by Yasuhara Chemical Co., Ltd.) and the like. These may be used in combination.

Note that, the content of the resin is generally in the range of 10 to 50% by mass, for example, 15 to 40% by mass, when the total mass of the adhesive layer is set to 100% by mass. In the case where the content of the resin is too small, the skin adhesiveness will become inferior, whereas if it is excessive, skin irritation increases, so care should be given. When the total mass of the adhesive layer is set to 100% by mass, the content of the resin can preferably be in the range of 20 to 40% by mass, for example 25 to 35% by mass, 27 to 33% by mass, alternatively 30 to 40% by mass.

[Softener]

In the adhesive layer of the nonaqueous adhesive skin patch of the present invention, softeners may be used to improve the handleability of adhesives.

Examples of the softeners (plasticizer) include petroleum-based softeners such as liquid paraffin, liquid rubber-based softeners such as liquid polyisoprene and polybutene, dibasic acid ester plasticizers such as phthalate ester and adipate, and other plasticizers such as polyethylene glycol, citrate, and the like. Among them, the liquid paraffin is preferably used because it is excellent in compatibility with elastomer-based adhesives, and there is no possibility of lowering the cohesive force thereof. For example, as the commercial product, Hicall M series (Registered trademark, liquid paraffin manufactured by Kaneda Co., Ltd.) and the like may be mentioned.

From the viewpoint of adhesiveness, the content of these softeners is generally in the range of 20 to 50% by mass, preferably 25 to 35% by mass, for example 27 to 35% by mass, alternatively 26 to 35% by mass, 26 to 32% by mass, and the like, when the total mass of adhesive layer is set to 100% by mass. When the blended amount of the softener is excessive, and if the backing film is, for example knitted fabric, there is fear that the softener may be permeated to the back side of the adhesive layer, causing inferiority in its stability. On the other hand, if the blended amount is too small, there is a possibility that skin irritation occurs, so care should be taken.

[Organic Acids]

In the adhesive layer of the nonaqueous adhesive skin patch of the present invention, organic acids are used in order to reduce skin irritation and to appropriately control the permeation amount of local anesthetics into the skin.

Examples of the organic acids include an oxalic acid, malonic acid, succinic acid, glutaric acid, adipic acid, sebacic acid, malic acid, tartaric acid, maleic acid, fumaric acid, citric acid, isocitric acid, benzoic acid, p-hydroxybenzoic acid, salicylic acid, acetylsalicylic acid, cinnamic acid, alkylsulfonic acids such as a methanesulfonic acid, ethanesulfonic acid and the like, aromatic sulfonic acids such as a benzenesulfonic acid, toluenesulfonic acid, dodecylbenzenesulfonic acid and the like.

Among those organic acids, divalent to trivalent organic acids are preferably used from the viewpoints of handle easiness, availability, control easiness of the transdermal absorption of lidocaine, adhesion properties, irritation reduction of skin, and the like. Especially, the citric acid or the tartaric acid will be preferable.

The blending amount of the organic acids is not particularly limited, but it is generally in the range of 0.3 to 10% by mass, for example, 0.3 to 4.0% by mass or 0.5 to 2.0% by mass, when the total mass of the adhesive layer is set to 100% by mass. Particularly, in the case of the tartaric acid, the blending amount thereof can be preferably 0.3 to 0.8% by mass, for example, 0.4 to 0.7% by mass, alternatively 0.4 to 0.6% by mass. Although it depends on the size (area) of the nonaqueous adhesive skin patch of the present invention, the blending amount of the organic acid per preparation will be preferably 10 to 84 mg, more preferably 12 to 42 mg or 14 to 42 mg, but more preferably 12 to 25 mg or 15 to 23 mg.

By blending the appropriate amount of organic acids, it enables the adhesive layer to be weakly acid. This reduces not only skin irritation but also the excessive skin permeation of medication. Note that, if the blending amount of organic acids is excessive, the skin permeation of medication will be excessively suppressed, so that the medication effects thereof on the adhesive skin patch may become low, so care should be taken.

0.01 to 5.0 mols, preferably 0.01 to 3.0 mols, more preferably 0.1 to 0.95 mols, alternatively 0.15 to 0.37 mols of the organic acid may be added to 1.0 mol of local anesthetics (e.g., lidocaine).

[Other Additives]

The adhesive layer of the nonaqueous adhesive skin patch of the present invention may further contain additives normally blended in the adhesive layer of the transdermal absorption preparation, for example, an antioxidant (oxidation inhibitor), filler, pigment, drug stabilizer, drug-solubility improver or drug solubility inhibitor. These additives are preferably the ones that exclude an oxidation inhibitor and transdermal absorption accelerant. The additives may be used individually or in combination of two or more kinds thereof. Note that, when containing the additives, care should be taken for not increasing the residual ratio thereof, in addition to the effects on the skin permeability. Specifically, it is preferable that any surfactant is not added when considering the skin irritation and residual rate.

Note that the transdermal absorption accelerant commonly used includes, for example, an aliphatic alcohol, fatty acid, fatty acid ester, alcoholamine, polyhydric alcohol alkyl ether, polyoxyethylene alkyl ether, glyceride (that is, fatty acid ester of glycerin), polyhydric alcohol medium chain fatty acid ester, lactic acid alkyl ester, dibasic acid alkyl ester, acylated amino acid, pyrrolidone and the like. The transdermal absorption accelerant is commonly used individually or in combination of two or more kinds thereof, but as mentioned above, it is preferable not to use the accelerant in the present invention.

As one example of the nonaqueous adhesive layer composition of the present invention, when the total mass of the adhesive layer is set to 100% by mass, 20 to 40% by mass of a rubber-based elastomer, 20 to 40% by mass of resin, 20 to 35% by mass of softener, 3.0 to 7.0% by mass of medication (particularly in the case of lidocaine) and 0.5 to 4.0% by mass of organic acid may be blended.

For example, when the total mass of the adhesive layer is set to 100% by mass, it can be proposed that 25 to 40% by mass of a rubber-based elastomer, 25 to 35% by mass of resin, 25 to 35% by mass of softener, 3.5 to 6.0% by mass of medication (particularly in the case of lidocaine) and 0.5 to 4.0% by mass of organic acid may be blended.

As one preferable embodiment, when the total mass of the adhesive layer is set to 100% by mass, it is proposed that 25 to 35% by mass of a rubber-based elastomer, 30 to 40% by mass of resin, 25 to 35% by mass of softener, 3.5 to 6.0% by mass of medication (particularly in the case of lidocaine) and 0.5 to 4.0% by mass of organic acid may be blended.

In another embodiment, when the total mass of the adhesive layer is set to 100% by mass, it is possible that 30 to 35% by mass of a rubber-based elastomer, 27 to 33% by mass of resin, 27 to 33% by mass of softener, 4.0 to 6.0% by mass of medication (particularly in the case of lidocaine) and 0.7 to 2.0% by mass of organic acid may be blended.

In yet another embodiment, when the total mass of the adhesive layer is set to 100% by mass, it is possible that 35 to 40% by mass of a rubber-based elastomer, 27 to 33% by mass of resin, 26 to 32% by mass of softener, 4.0 to 6.0% by mass of medication (particularly in the case of lidocaine) and 0.6 to 2.0% by mass of organic acid may be blended.

<Backing Film>

Examples of the backing film used in the adhesive skin patch of the present invention are: papers such as impregnated paper, coated paper, high-quality paper, kraft paper, Japanese paper, glassine paper; plastic films such as polyester films, for example, polyethylene terephthalate, polybutylene terephthalate and the like, polyolefin films, for example, polyethylene, polypropylene and the like, polyvinyl chloride film, polycarbonate film, polyurethane film, cellophane film; foam; fabric such as nonwoven fabric, woven fabric, knitted fabric; and a laminated body comprising two or more of the above. The materials of fabric such as a nonwoven fabric, woven fabric, knitted fabric and the like may be mentioned as polyester, polyurethane, polyethylene, polypropylene and the like.

In the adhesive skin patch at which the present invention aims, for example, fabrics selected from the group consisting of a nonwoven fabric, woven fabric, knitted fabric can be preferably used. Further, the backing film made of at least one material selected from the group consisting of polyesters such as polyethylene terephthalate and polybutylene terephthalate, and polyolefins such as polyethylene and polypropylene can be preferably used.

Among them, the materials satisfying the following will be preferable: that is, local anesthetics contained in the adhesive layer are not absorbed into the patch; local anesthetics will not be discharged from the side of the backing film; the patch is allowed to be well affixed to the skin; the material is soft enough to follow the movement of skin; and skin rashes are suppressible even after the prolonged affixation of the patch to the skin. Knitted cloth, specifically polyester knitted cloth, will be preferable when considering no adsorption of medication, high followability to the movement of the skin surfaces to which the patch is affixed.

The backing film may be colored into skin tones with colorant, so that it can reduce the disparity between the patch color and skin when affixed. Examples of the colorant include pigments, organic pigments, natural pigments and the like.

The thickness of the backing film may be optionally selected in consideration of a stretch, tensile strength, physical properties such as workability, feeling when affixed, sealability over wounded portions, the transition of medication to the backing film, etc. However, the thickness thereof is normally 5 μm to 1 mm.

When the backing film is cloth, its thickness is preferably 50 μm to 1 mm, more preferably 100 to 800 μm, further preferably 200 to 700 μm. From the viewpoint of the skin followability, the weight per unit area of the backing film is preferably 300 g/m$^2$ or less, more preferably 200 g/m$^2$ or less, and further preferably 150 g/m$^2$ or less.

Further, the backing film may contain additives such as an antistatic agent and ultraviolet inhibitor to such an extent that the effects on the present invention is not impaired. Examples of the antistatic agent include surfactants (anionic surfactant, cationic surfactant, nonionic surfactant, amphoteric surfactant) and the like. By using the antistatic agent, it can overcome the anchoring of the backing film and some defects caused in processes.

<Separator Layer>

The nonaqueous adhesive skin patch of the present invention at least has the backing film and the adhesive layer placed thereabove, but a separator layer may be provided if necessary. In many cases, the adhesive skin patch normally has the layer structure configured by: Backing film/Adhesive layer/Separator layer.

The term "separator layer" refers to the layer which: protects the adhesive layer, for example, a styrene thermoplastic elastomer adhesive layer, until the nonaqueous adhesive skin patch is affixed to the skin; prevents the adhesive layer from being deteriorated; and is to be removed from the adhesive layer (also referred to as a release layer or release liner) when the nonaqueous adhesive skin patch is affixed to the skin. The separator layer may be the one commonly used in nonaqueous adhesive skin patches. It is preferable that the separator layer is made of the material not easily absorbing or adsorbing local anesthetics in the adhesive layer. The separator layer can be properly selected in consideration of releasability from the adhesive layer or flexibility thereof. For example, the following uncolored or colored sheet may be used as the separator layer, that is: plastic films such as polyethylene terephthalate (PET), polybutylene terephthalate, polyethylene naphthalate, unstretched polypropylene, drawn polypropylene, polyethylene, polyurethane, polyvinyl chloride, polystyrene and the like; silicone-processed papers that has been silicone-processed to synthetic resin, synthetic paper, synthetic fibers and the like; and laminated papers and the like on which polyethylene, etc. are laminated on aluminum foil or kraft paper. Particularly, release-treated resin films such as a silicone-treated PET film, silicone-treated polypropylene film, silicone-treated polyethylene film, fluororesin-coated PET film, fluororesin-coated polypropylene film, and a fluororesin-coated polyethylene film are preferably used as the separator layer. Further, the laminate comprising these release-treated resin films and papers, the resin films on which aluminum is vapor-deposited, the papers coated with silicone oil or the like may be used. Note that release-treatments over the separator layer may be applied not only to the adhesive layer surface but also to the surface placed opposite to the adhesive layer. For easily taking out the nonaqueous adhesive skin patch from the packaging material, convexo-concave configurations may be provided on one side or both sides of the separator layer. Further, the shape of the separator layer may be a square, rectangular, circular, etc., and some rounded corners may be provided if desired. The size of the separator layer may be the same as the size of the backing film in the adhesive skin patch or slightly larger. The separator layer may be composed of one individual piece or may be divided into a plurality of pieces, and breaks may be formed by a straight line, wavy line or sewing line shape. It is possible that a portion between each separator layer may be overlapped to each other. The thickness of the separator layer is not particularly limited, but it is normally in the range of 10 μm to 1 mm, preferably 20 to 500 μm, and more preferably 40 to 200 μm.

<Thickness of Adhesive Layer>

The thickness of the adhesive layer in the nonaqueous adhesive skin patch of the present invention is normally in the range of 20 to 500 μm, preferably 30 to 400 μm, more preferably 35 to 300 μm, further preferably 40 to 200 μm.

If the thickness of the adhesive layer is too small, tackiness to the skin may become insufficient, the local anesthetic content (absolute amount) may become small, and absorption durability to the skin may become inadequate. On the other hand, if the thickness of the adhesive layer is too large, the large amount of adhesive may remain on the skin when releasing the patch. This will deteriorate the handleability of the patch. Further, in the production of the adhesive skin patch, when the adhesive layer is subjected to a coating process through a dissolution method (or a dissolution coating method), and if the thickness of the adhesive layer is large, there is a possibility that solvents may remain, thus increasing skin irritation.

In addition, when the adhesive layer is shown based on mass per unit area, it can be normally 10 to 1000 $g/m^2$, preferably 50 to 500 $g/m^2$, for example 100 to 300 $g/m^2$ or 100 to 200 $g/m^2$.

In the nonaqueous adhesive skin patch of the present invention, the thickness of the adhesive layer can be made further thinner as compared with the conventional adhesive layers of local-anesthetic containing adhesive skin patches using nonaqueous adhesive skin patches.

Therefore, the blending amount of each component per unit area (eventually per one preparation), particularly the local anesthetics and organic acids, can notably decrease than before.

<Cumulative Permeation Amount>

Considering the nonaqueous adhesive skin patch of the present invention, in the nature of the preparation, the medication needs not to wear off until the end of the applied period, within the assumed application period (the period the patch is affixed), and the appropriate amount of medication is required to continuously permeate (infiltrate) into the skin.

In the purpose of the adhesive skin patch, the cumulative permeation amount of medication after 12 hours since application is preferably in that the cumulative permeation amount of medication, especially lidocaine, after 12 hours is in the range of 50 to 210 $\mu g/cm^2$, for example, about 120 to 200 $\mu g/cm^2$, especially 150 to 200 $\mu g/cm^2$.

<Method for Producing Adhesive Skin Patch>

The method for producing the nonaqueous adhesive skin patch, at which the present invention aims, is not particularly limited. For example, it is possible to adopt a hot-melt method, calendar method, dissolution method, or the like, each of which is the common production method of the adhesive skin patch. In the nonaqueous adhesive skin patch of the present invention, the term "nonaqueous" means that moisture is not intentionally added into the adhesive layer (a plaster) through the production processes.

The following is the one example of the method for producing the adhesive skin patch by the hot-melt method. First, a rubber-based elastomer, resin, softening agent, other additives and the like are heated and stirred at high speed by means of a heat-controllable and high-speed rotary mixer in a nitrogen atmosphere at 100 to 200° C. adhesive (plaster) temperature for 20 to 100 minutes, so as to obtain a molten material. Thereafter, a local anesthetic and organic acid are added into the molten material, and then the molten material is further heated and stirred at high speed at the plaster temperature of 100 to 150° C. for 5 to 30 minutes, so as to obtain an adhesive in which each component therein is uniformly arranged. Note that the above-described temperature and time defined by the stir of the above are examples, so that the present invention is not limited to the range thereof.

By using a hot melt coating machine, the adhesive (plaster) that has been obtained through the above method is extruded from a die head portion that is temperature-controlled at 100 to 150° C. The extruded adhesive is then spread on the separator layer in such a manner that the application amount of the adhesive becomes, for example, 100 to 300 $g/m^2$. The backing film is then laminated thereon and cut into a predetermined shape, so as to produce the adhesive skin patch.

The shape of the nonaqueous adhesive skin patch is not particularly limited but may be selected from various shapes in accordance with the sites to be applied, the shape possibly being quadrate (square, rectangle, etc.), quadrangle (trapezoid, rhombus, etc.), polygon, circle, ellipse, semicircle, triangle, crescent, or shapes in combination of these.

The size of the adhesive skin patch can be suitably determined. However, when taking account of the administration purpose of medication, the dosage of medication, minimizing the quantity of medication to be adhered to the backing film through the volatilization of medication in the packaging material, and the easy affixation of the patch, the adhesive skin patch may be, for example, about 40 $cm^2$ to 240 $cm^2$, preferably 70 $cm^2$ to 140 $cm^2$. The blending amount of organic acid per preparation as described above may be the blended amount per preparation having the size defined within the above numerical ranges.

It should be noted that the nonaqueous adhesive skin patch of the present invention prepared as described above is preferably stored in the package made of the material having a high-sealing property and high light-shielding property. The nonaqueous adhesive skin patch will be preferably stored therein until just before use.

As packaging materials with the high-sealing property and high-light shielding property used for the above-mentioned packaging, any material commonly used for the packaging of packaging adhesive skin patches may be applied. Examples of the high-sealing packaging materials include polyolefin-based resin films such as polyethylene film, polypropylene film and polymethylpentene film; cyclic polyolefin-based resin film; vinyl-based resin films such as polyvinyl chloride film, polyvinylidene chloride film, polyvinyl alcohol film, polystyrene film, polyacrylonitrile film and ionomer film; ethylene-vinyl alcohol copolymer (EVOH) film; polyester-based resin films such as polyethylene terephthalate film; polyamide-based resin films such as nylon film; cellulose-based resin films such as cellophane; a polycarbonate resin film, and a laminated film made thereby. In addition to the sealing property, for also increasing the light-shielding property, the packaging materials of the following can be used: the laminated film defined by the above resin film (or the laminated film of those resin films) and aluminum; a pigment-added resin film where a black pigment or the like is added to the resin film of the above. The resin film(s), the laminated film thereof, and the like may be used in various combinations (by being laminated).

The nonaqueous adhesive skin patch is stored in the package made of the above packaging materials, and if necessary, nitrogen replacement may be carried out in the package, or gas within the package may be reduced. The patch may be stored by any commonly known method such as heat sealing.

[Administration Method]

The frequency of administering the nonaqueous adhesive skin patch of the present invention is, for example, up to 3 pieces per day, or 1 to 2 times of medication per day. The period for the administration may be, for example, up to 12 hours. The patch may be applied to the skin as needed for any time from morning till night. For example, the patch may be applied at 7 o'clock in the morning and removed at 7 o'clock in the evening, or the patch may be applied at 8 o'clock in the evening after taking a bath and removed at 8 o'clock in the next morning.

In particular, the nonaqueous adhesive skin patch of the present invention can be suitably applied to postherpetic neuralgia.

[Embodiment]

Hereinafter, the present invention will be specifically described with reference to embodiments and comparative embodiments, but the present invention is not limited to those embodiments.

Embodiment 1

Through the hot-melt method described in <Method for Producing Adhesive Skin Patch>, in accordance with Table 1, the heating stir was performed in the following formulation (the numerical values (% by mass) indicate the ones where the total mass of the adhesive layer is set to 100% by mass, the same shall apply below): 5.0% by mass of lidocaine as a local anesthetic; 0.5% by mass of a citric acid as organic acids; 22.0% by mass of a styrene-based thermoplastic elastomer (SIS): SIS5002 [Styrene content 22% by mass, Diblock ratio: 15% by mass, manufactured by JSR Corporation] and 10.0% by mass of polyisobutylene (PIB): OppanolB-12SFN (manufactured by BASF Japan KK) as elastomers; 31.5% by mass of Pine Crystal KE-311 as resins [hydrogenated rosin glycerin ester, manufactured by Arakawa Chemical Industries, Ltd.]; and 31.5% by mass of Hicall (Registered trademark) M-352 (liquid paraffin, manufactured by Kaneda Co., Ltd.). Through the above, the uniform adhesive compositions have been prepared. In the heating stirring, the materials, besides lidocaine and organic acids, were mixed in the Henschel mixer in the nitrogen atmosphere at the temperature of 170° C. and the rotational speed of 600 rpm. After the mixture became uniform, the temperature was set to 140° C. Lidocaine and organic acids were then added thereinto and stirred in the condition of the rotational speed of 200 rpm for 15 minutes.

Subsequently, the adhesive composition was spread on the silicone-treated polyester film (75 μm in thickness, a release film) to have the plaster mass of 150 g/m² thickness, so as to form the adhesive layer. Above the adhesive layer, the polyester-based knitted fabric as the backing film (circular knit, the basis weight of about 100 g/m², about 500 μm thickness) was laminated and cut into the pieces of 140 cm², so as to prepare the adhesive skin patch.

Embodiments 2 to 12

In accordance with the formulation of Table 1, the adhesive skin patch was prepared in the same procedure as shown in Example 1 of the above.

Comparative Embodiments 1 to 7

In accordance with the formulation of Table 2, the adhesive skin patch was prepared by the same procedure as shown in Example 1 of the above.

Note that, in these embodiments and comparative embodiments, other than the above components, YS resin PX 1150 N (terpene resin, manufactured by Yasuhara Chemical Co., Ltd.) was used as resin. Further, a tartaric acid was also used as the organic acid, in addition to the above components.

<Performance Evaluation of Nonaqueous Adhesive Skin Patch>

Each performance of the adhesive skin patches (hereinafter referred to as test preparation) that has been arranged in Embodiments 1 to 12 and Comparative Embodiments 1 to 7 was evaluated by the following methods (1) to (3), respectively. The results obtained are shown in Table 1 and Table 2.

(1) Evaluation of Skin Permeation Amount

Regarding the skin permeation amount of lidocaine as a local anesthetic, the in-vitro permeation test was carried out.

The abdominal skin of the hairless mouse (male, 7 weeks old) was mounted on the horizontal diffusion cell of 10 mL capacity with the diameter of 20 mmφ. Warm water at 32° C. was circulated in the double-structured cell, the interior of the cell being kept at a constant temperature condition. Each test preparation punched out into 15 mmφ was attached on the stratum corneum side of the skin. Approximately 10 mL of purified water was filled on the receiver side. While stirring the purified water with a stirring bar, 0.5 mL of the water was chronologically sampled every 2 hours up to 12 hours. 0.5 mL of methanol was added to each sampled specimen, and the mixture was stirred and centrifuged. The deproteinized solution was then quantified by HPLC (High Performance Liquid Chromatography), and the medication concentration thereof was measured to determine the skin permeation amount of lidocaine. The same amount of purified water was then supplemented to the receiver solution after sampled. The average value of n=3 was then obtained.

The above evaluation had been carried out on each test preparation within one week since the test preparation was produced, at a normal temperature (20° C.±5° C.). Each cumulative permeation amount of 2 hours and 12 hours after the start of the permeation test is shown in Table 1 and Table 2.

In addition, in the test preparation that has been stored at 60° C. for two weeks after produced, the cumulative permeation amount after 12 hours from the start of the permeation test is also shown in Table 1 and Table 2.

(2) Measurement of Keratin Remove Amount

Each test preparation of the above was punched into 10×30 mm to obtain a specimen. This specimen was affixed to the skin on the inner forearm of each testee (total of 8 in their 20s to 60s, both sexes) for 12 hours, and then removed. The removed specimen was then immersed in the following stain solution for 4 hours to stain keratinocytes. The specimen was then cleansed with distilled water. The amount of keratin (the stained portions), which was moved from the skin to the adhesive surface of the removed specimen, was observed with an optical microscope. The remove amount of keratinocytes was then measured per the total area (%) occupied, and the average value was determined. The obtained results are shown in Table 1 and Table 2.

Note that, when the remove amount of keratin is 100%, it means that keratinocytes are adhering to the whole surface of the adhesive skin patch.

Stain solution composition:

Gentian Violet 1.0%

Brilliant Green 0.5%

Distilled water 98.5%

(3) Determination of pH Values

Each pH test paper was placed on the adhesive layer (a plaster layer) of the adhesive skin patch of each Embodiment and Comparative Embodiment. One drop of distilled water was then dropped on the pH test paper, and the pH value was determined based on color changes identified by the pH test paper.

The obtained results are shown in Table 1 and Table 2.

TABLE 1

| | EMBODIMENTS | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Elastomer (SIS): SIS5002 | 22 | 22 | 22 | 22 | 22 | 28 | 27.9 | 27.5 | 26.9 | 22 | 22 | 22 |
| Elastomer (PIB): Oppanol B-12SFN | 10 | 10 | 10 | 10 | 10 | 10 | 10 | 10 | 10 | 10 | 10 | 10 |
| Softener: Hicall M-352 | 31 | 30.8 | 30.5 | 29.5 | 30.5 | 26 | 26 | 26 | 26 | 30.9 | 30.7 | 30.33 |
| Resin: Pine Crystal KE-311 | 31.5 | 31.5 | 31.5 | 31.5 | 31.5 | 31.5 | 31.5 | 31.5 | 31.5 | 31.5 | 31.5 | 31.5 |
| Resin: YS resin PX 1150 | 0 | 0 | 0 | 0 | 0 | 0 | 0 | 0 | 0 | 0 | 0 | 0 |
| Organic acid: Citric acid | 0.5 | 0.7 | 1 | 2 | 0 | 0 | 0 | 0 | 0 | 0 | 0 | 0 |
| Organic acid: Tartaric acid | 0 | 0 | 0 | 0 | 1 | 0.5 | 0.6 | 1 | 0.6 | 0.6 | 0.8 | 1.17 |
| Local anesthetic: Lidocaine | 5 | 5 | 5 | 5 | 5 | 4 | 4 | 4 | 5 | 5 | 5 | 5 |
| Total (% by mass) | 100.0 | 100.0 | 100.0 | 100.0 | 100.0 | 100.0 | 100.0 | 100.0 | 100.0 | 100.0 | 100.0 | 100.0 |
| Plaster mass (g/m$^2$) | 150 | 150 | 150 | 150 | 150 | 150 | 150 | 150 | 150 | 150 | 150 | 150 |
| Lidocaine ($\times 10^{-5}$ mol/cm$^2$) | 0.32 | 0.32 | 0.32 | 0.32 | 0.32 | 0.256 | 0.256 | 0.256 | 0.32 | 0.32 | 0.32 | 0.32 |
| Molar ratio: Organic acid/Local anesthetic | 0.12 | 0.17 | 0.24 | 0.49 | 0.31 | 0.195 | 0.234 | 0.390 | 0.187 | 0.187 | 0.2498 | 0.3654 |
| Organic acid (per mg/1 preparation)※ | 10.5 | 14.7 | 21 | 42 | 21 | 10.5 | 12.6 | 21 | 12.6 | 12.6 | 16.8 | 24.57 |
| 2 hr cumulative permeation (μg/cm$^2$) | 23 | 21 | 19 | 15 | 18 | 15 | 13 | 13 | 20 | 21 | 20 | 13 |
| 12 hr cumulative permeation (μg/cm$^2$) | 208 | 200 | 186 | 150 | 164 | 150 | 147 | 123 | 199 | 180 | 162 | 122 |
| 12 hr cumulative permeation after 2 weeks storage at 60° C. (μg/cm$^2$) | 204 | 194 | 174 | 160 | 155 | 143 | 139 | 117 | 185 | 175 | 162 | 115 |
| Keratin removal (area) (%) | 5 | 5 | 5 | 5 | 5 | 9 | 10 | 9 | 8 | 5 | 6 | 7 |
| pH value | 6 | 6 | 6 | 6 | 6 | 6 | 6 | 6 | 6 | 6 | 6 | 6 |

※per 1 preparation: applied on the adhesive layer at the amount of plaster mass of Table 1 and cut into 140 cm$^2$

TABLE 2

| | COMPARATIVE EMBODIMENTS | | | | | | |
|---|---|---|---|---|---|---|---|
| | 1 | 2 | 3 | 4 | 5 | 6 | 7 |
| Elastomer (SIS): SIS5002 | 22 | 17 | 17 | 30 | 22 | 22 | 22 |
| Elastomer (PIB): Oppanol B-12SFN | 10 | 5 | 5 | 10 | 10 | 0 | 0 |
| Softener: Hicall M-352 | 35.5 | 31 | 34 | 13 | 27.4 | 26 | 41 |
| Resin: Pine Crystal KE-311 | 0 | 11 | 16 | 27 | 31.5 | 45 | 30 |
| Resin: YS resin PX 1150 | 27.5 | 33 | 25 | 15 | 0 | 0 | 0 |
| Organic acid: Citric acid | 0 | 0 | 0 | 0 | 4.1 | 2 | 2 |
| Organic acid: Tartaric acid | 0 | 0 | 0 | 0 | 0 | 0 | 0 |
| Local anesthetic: Lidocaine | 5 | 3 | 3 | 5 | 5 | 5 | 5 |
| Total (% by mass) | 100.0 | 100.0 | 100.0 | 100.0 | 100.0 | 100.0 | 100.0 |
| Plaster mass (g/m$^2$) | 150 | 200 | 200 | 100 | 150 | 150 | 150 |
| Lidocaine ($\times 10^{-5}$ mol/cm$^2$) | 0.32 | 0.19 | 0.19 | 0.32 | 0.32 | 0.32 | 0.32 |
| Molar ratio: Organic acid/Local anesthetic | 0 | 0 | 0 | 0 | 1.00 | 0.49 | 0.49 |
| Organic acid (per mg/1 preparation)※ | 0 | 0 | 0 | 0 | 66.1 | 42 | 42 |
| 2 hr cumulative permeation (μg/cm$^2$) | 45 | 20 | 20 | 19 | 2 | — | 15 |
| 12 hr cumulative permeation (μg/cm$^2$) | 380 | 190 | 204 | 198 | 54 | — | 151 |
| 12 hr cumulative permeation after 2 weeks storage at 60° C. (μg/cm$^2$) | 360 | 144 | 183 | 162 | 59 | — | 73 |
| Keratin removal (area) (%) | 4 | 72 | 66 | 64 | 6 | 85 | 4 |
| pH value | 7 | 7 | 7 | 7 | 6 | 6 | 6 |

※per 1 preparation: applied on the adhesive layer at the amount of plaster mass of Table 2 and cut into 140 cm$^2$ As shown in Table 1, considering each adhesive skin patch of Embodiments 1 to 12, both the cumulative permeation amount after 12 hours and the cumulative permeation amount after 12 hours in the condition that the patch has been stored for 2 weeks at 60° C. were in the range of about 120 to 200 μg/cm$^2$. Especially, each adhesive skin patch of Embodiments 2 to 5 and Embodiments 9 to 11 was in the range of 150 to 200 μg/cm$^2$, so that it was confirmed that the patch not only allowed to obtain the continuous administration of local anesthetics but also achieved excellent storage stability. Further, the remove amount of keratin (area) of the adhesive skin patch was limited up to 5% to 10%, and the pH value of the adhesive layer thereof showed the value of 6 (that is, weak acidity). Accordingly, it was confirmed that each adhesive skin patch of the above could reduce skin irritation.

On the other hand, in Comparative Embodiment 1 where organic acids were not added, the cumulative permeation amount of local anesthetics after 12 hours became excessive. Further, in Comparative Embodiments 2 to 4 and 6, in which the blending amount of resin was 40% by mass or more, the remove amount of keratin (area) became extremely large, that is, more than 60%, consequently causing high skin irritation when removing the patch. Especially in Comparative Embodiment 6, the remove amount of keratin became extremely large, that is, 85%, and the adhesion of the patch became excessively high. Accordingly, with no need to evaluate the skin permeation amount, it was confirmed that the patch concerned was inappropriate for actual use. Moreover, in Comparative Example 5, in which the organic acid was excessively blended, it was resulted in that the permeation amount of local anesthetic was largely suppressed. Further, in Comparative Example 7, in which the softener was excessively blended, the cumulative permeation amount of the test specimen that has been stored for 2 weeks at 60° C. was greatly reduced after 12 hours. The storage stability thus became inferior.

The invention claimed is:

1. A nonaqueous adhesive skin patch at least comprising a backing film and an adhesive layer placed thereabove, the adhesive layer containing a local anesthetic, wherein
when the total mass of the adhesive layer is set to 100% by mass, the adhesive layer includes the following:
20 to 40% by mass of an elastomer comprising a styrene-based thermoplastic elastomer and polyisobutylene;
20 to 35% by mass of a softener comprising liquid paraffin;
20 to 40% by mass of a resin comprising a hydrogenated rosin glycerin ester or a terpene resin;
3.0 to 7.0% by mass of the local anesthetic, wherein the local anesthetic comprises lidocaine; and
0.3 to 4.0% by mass of a divalent or trivalent organic acid comprising citric acid or tartaric acid,
and wherein the adhesive layer has a mass per unit area of 100 to 200 $g/m^2$.

2. The nonaqueous adhesive skin patch according to claim 1, wherein the adhesive layer contains 25 to 35% by mass of the softener and 30 to 40% by mass of the resin.

3. The nonaqueous adhesive skin patch according to claim 1, wherein the adhesive skin patch contains the local anesthetic in an amount such that a cumulative permeation amount of the local anesthetic after an elapse of 12 hours since application is 120 to 200 $\mu g/cm^2$.

4. The nonaqueous adhesive skin patch according to claim 1, wherein the adhesive skin patch contains the local anesthetic in an amount such that a cumulative permeation amount of the local anesthetic after an elapse of 12 hours since application is 150 to 200 $\mu g/cm^2$.

5. The nonaqueous adhesive skin patch according to claim 1, wherein the adhesive layer does not contain an antioxidant and a transdermal absorption accelerant.

6. The nonaqueous adhesive skin patch according to claim 1, wherein the patch is applicable for postherpetic neuralgia.

7. The nonaqueous adhesive skin patch according to claim 1, wherein the backing film is a polyester knit fabric.

8. The nonaqueous adhesive skin patch according to claim 1, wherein 10 to 84 mg of the organic acid is blended per one preparation of the nonaqueous adhesive skin patch.

* * * * *